US006497151B1

(12) United States Patent
Watts et al.

(10) Patent No.: US 6,497,151 B1
(45) Date of Patent: Dec. 24, 2002

(54) NON-DESTRUCTIVE TESTING METHOD AND APPARATUS TO DETERMINE MICROSTRUCTURE OF FERROUS METAL OBJECTS

(75) Inventors: Kenneth J. Watts, Jefferson County, AL (US); David M. Winslett, Hueytown, AL (US)

(73) Assignee: U.S. Pipe & Foundry Company, Fairfield, AL (US)

( * ) Notice: Subject to any disclaimer, the term of this patent is extended or adjusted under 35 U.S.C. 154(b) by 0 days.

(21) Appl. No.: 09/467,314

(22) Filed: Dec. 20, 1999

(51) Int. Cl.[7] ............................................... G01N 29/24
(52) U.S. Cl. .......................................... 73/622; 73/643
(58) Field of Search .......................... 73/643, 579, 584, 73/596, 602, 627, 628, 577, 578, 644, 617, 624, 598, 573; 324/242, 240, 220

(56) References Cited

U.S. PATENT DOCUMENTS

| 4,002,058 | A | * | 1/1977 | Wolfinger | 73/578 |
|---|---|---|---|---|---|
| 4,165,649 | A | * | 8/1979 | Greer, Jr. | 73/644 |
| 4,481,824 | A | * | 11/1984 | Fujimoto et al. | 73/643 |
| 4,543,827 | A | * | 10/1985 | Tominaga et al. | 73/602 |
| 5,161,521 | A | * | 11/1992 | Kasahara et al. | 73/576 |
| 5,581,037 | A | * | 12/1996 | Kwun et al. | 73/623 |
| 5,612,495 | A | * | 3/1997 | Shimada et al. | 73/579 |

* cited by examiner

*Primary Examiner*—Helen Kwok
(74) *Attorney, Agent, or Firm*—Bradley Arant Rose & White, LLP; Thad G. Long; Margaret Smith Kubiszyn

(57) ABSTRACT

A non-destructive testing method and apparatus for determining the microstructure of ferrous metal objects, such as cast iron pipe. A sonic wave is induced into the metal object by magnetostriction. A sensor assembly captures the acoustic energy induced in the metal object and sends a signal output to signal processing electronics. The electronics amplify the signal. The amplified signal is then captured by the data acquisition system and analyzed by the data analysis system. The data analysis system may calculate the energy of the acoustic wave or calculate the time from the initial induction of the sonic wave to the Villari reversal point to determine nodularity of the metal object.

1 Claim, 7 Drawing Sheets

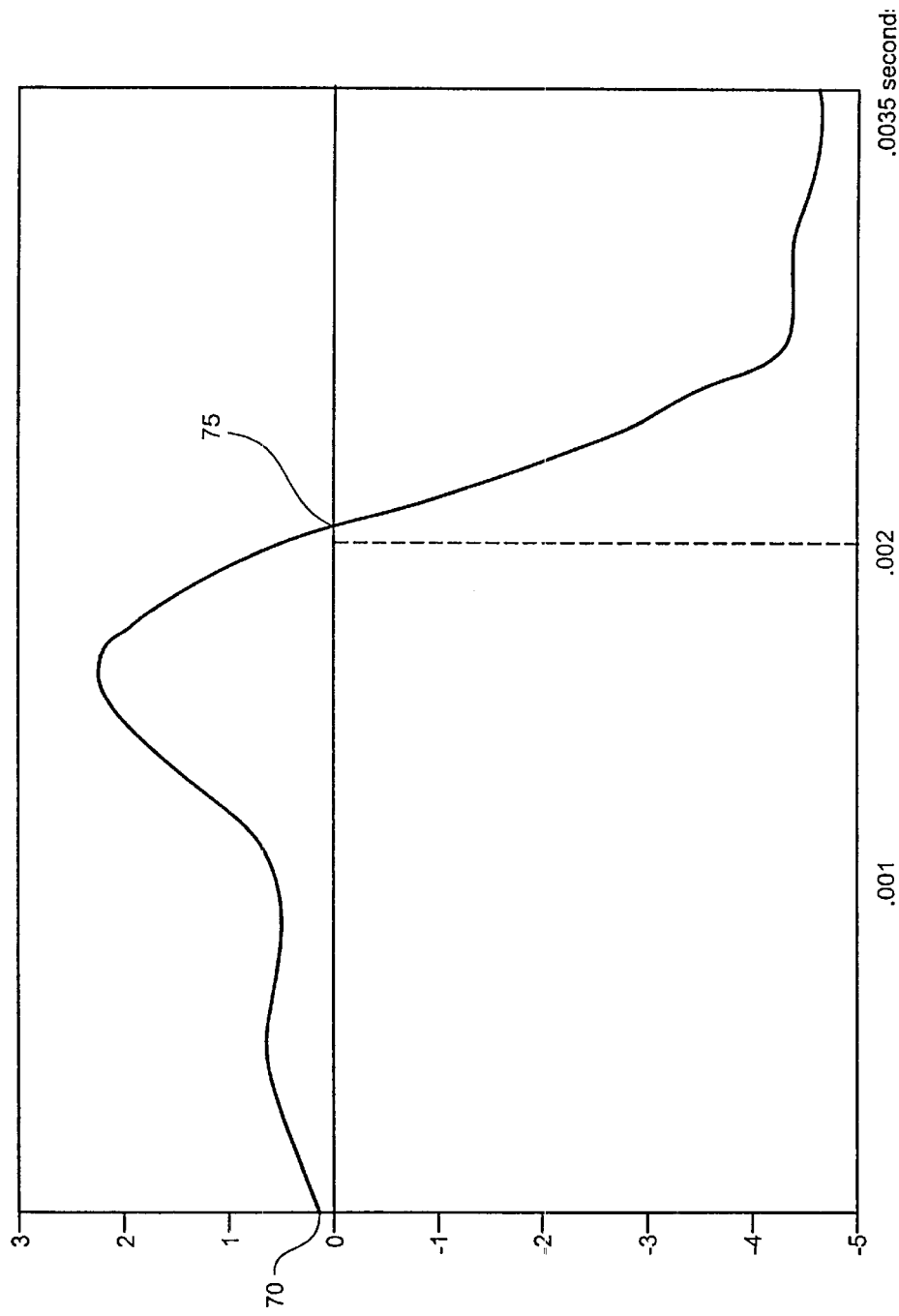

NON-DESTRUCTIVE TESTING METHOD AND APPARATUS TO DETERMINE MICROSTRUCTURE OF FERROUS METAL OBJECTS

BACKGROUND

This present invention relates to the field of non-destructive testing methods and apparatuses, specifically to non-destructive testing methods and apparatuses to determine metallurgical and physical properties of a ferrous test subject. Iron pipe centrifugally cast from ductile iron will be used as the exemplary test subject throughout this disclosure. Ductile iron is made by treating a low sulfur cast iron with magnesium, which causes the graphite to form spheres or nodules rather than flakes. These nodules give ductile iron its desirable qualities, namely a high modulus of elasticity and, therefore, increased strength. If a certain period of time elapses after the treating with magnesium takes place and before the ductile iron is cast, the magnesium becomes bound up with other elements in the iron and is unable to form nodules. Cast iron in which the graphite forms into flakes is commonly called gray iron. Gray iron has a lower modulus of elasticity. The graphite structure may vary along the length of the pipe, containing both nodules and flakes. It is advantageous for the manufacturer of ductile iron pipe to test the pipe to determine if there is any questionable graphite structure or non-ductile areas along the length of the pipe.

It has been known that the modulus of elasticity in a ductile iron pipe can be determined by measuring the energy of an acoustic wave that has been generated in the pipe wall. The graphite in gray cast iron offers great resistance to the passage of sound waves and, thus, the velocity is lower than that of a sound wave passed through ductile iron. Various methods and apparatuses employing the concept that the velocity of sound waves can be measured to determine the modulus of elasticity in cast iron have been documented and patented.

Diamond, U.S. Pat. No. 3,603,136, discloses a method and apparatus for determining the nodularity of a workpiece as a function of the speed of sound waves through the workpiece. This is achieved by positioning the workpiece at a predetermined distance from an electro-acoustic transducer, or by positioning the casting between two electro-acoustic transducers which are spaced at a predetermined distance. The casting is immersed in water, an ultrasonic pulse is generated by a crystal immersed in the water and has sufficient energy so that it will pass through both the first and second surfaces of the workpiece. Back reflections are produced and the crystal generates signals upon reception of each back reflection. An oscilloscope displays the transmitted pulse and the first and second back reflections, allowing the operator to calculate the total time required for the impulse to travel from the first surface to the second surface. If the crystal is positioned a predetermined distance away from the second surface, the actual thickness of the casting is not required in subsequent calculations which then determine the velocity of sound in the workpiece solely as a function of the time between the display of the pulses.

DiLeo, U.S. Pat. No. 3,844,163, discloses an ultrasonic nondestructive testing system for measuring the velocity at which ultrasonic energy moves through a material. A pair of search units are provided for propagating ultrasonic energy towards the opposite sides of a workpiece and receiving such energy therefrom. A computer measures the various time delays resulting from the ultrasonic energy propagating thorough the workpiece and computes the velocity of the ultrasonic energy in the workpiece.

Bantz, et al., U.S. Pat. No. 3,848,460, also discloses a method of measuring the velocity of sound in a workpiece using transmit and receive ultrasonic transducers spaced a predetermined distance apart from each other in a liquid bath.

In the above references, generation of ultrasonic waves is achieved primarily by some form of electro-mechanical conversion, usually piezoelectricity. The disadvantage of this method of sonic measurement is that it requires a fluid couplant, such as a liquid bath, to mechanically transfer sound generated by the transducer into and out of the workpiece. As the workpiece must be covered with a thin layer of fluid or immersed in liquid, this process complicates testing, making it more expensive and time-consuming.

Buttram, et al., U.S. Pat. No. 5,714,688, discloses a method of examining ductile iron using an electromagnetic acoustic transducer (EMAT) system to determine a time-of-flight of an ultrasonic shear wave pulse transmitted through a casting at a selected location, from which a velocity of sound in the casting can be determined. EMATs are the basis of a non-contact ultrasonic inspection method which requires no fluid couplant because the sound is produced by an electromagnetic acoustic interaction within the material. The method disclosed in Buttram uses first and second EMATs arranged on opposite sides of the casting at a selected location. The thickness of the casting is measured at said location. The first EMAT is energized, thus creating and sending an ultrasonic pulse through the casting to the second EMAT. The pulse is received at the second EMAT and the time required for the pulse to travel through twice the thickness of the casting is measured. The shear wave velocity is calculated using the relationship between the thickness and the measured time value. The degree of nodularity in the casting is determined from a pre-established relationship between the shear wave velocity and the percent of nodularity for ductile cast iron.

Thus, Buttram discloses a method for determining ductility of a workpiece without the need for a fluid couplant, improving on the prior art. However, the method disclosed in Buttram requires a measurement to be made of the thickness of the workpiece at the particular location at which the transmission of the pulse is to occur. As such, a measurement can be cumbersome, time-consuming, and inaccurate in a manufacturing environment, it is desirable to implement a more accurate and efficient method for determining ductility of the workpiece without a requirement that such a thickness measurement be made.

Thus, there is a need for a non-destructive method and apparatus for efficiently and accurately determining the microstructure of ferrous metal objects that is suitable for a modem manufacturing environment, that does not require the workpiece to be immersed in a couplant and does not require the operator to know the thickness of the workpiece being tested.

SUMMARY OF THE INVENTION

The present invention provides a non-destructive method and apparatus for determining the microstructure of ferrous metal objects. More specifically, this method and apparatus will allow the user to measure metallurgical and physical properties of a ferrous object such as a cast iron pipe without the need for a couplant or for potentially inaccurate measurements. In the preferred embodiment, the apparatus is composed of a capacitive discharge magnetizer, one or more sensors, signal processing electronics, and a data analysis system. A sonic wave is introduced into the pipe wall by magnetostriction, as disclosed in Watts, et al., U.S. Pat. No. 5,336,998. In the preferred embodiment, the firing of the capacitive discharge magnetizer through a central conductor causes the pipe wall to contract. This contraction produces a sonic wave, which propagates through the pipe wall. Multiple reflections of the sonic wave take place, and the sensor(s) capture the intensity of the sonic waves. After processing through the electronics, the signal is analyzed by the computer software in the data analysis system. The time from the beginning of current discharge to the point at which the displacement of the pipe wall crosses an initial rest point, (the Villari Reversal Point), is measured and compared against a known value to determine ductility of the workpiece.

The present invention has many objects and advantages over the prior art. One such object is to provide a method for determining microstructure of a ferrous metal workpiece quickly and efficiently in a modern manufacturing environment.

A further object of the present invention is to provide a method and apparatus for determining the microstructure of a ferrous metal workpiece without the need for a fluid couplant, thus decreasing the time for testing and reducing the potential for inaccuracies in measurements due to contaminants in the couplant.

Yet another object of the present invention is to provide a method and apparatus for determining the microstructure of a ferrous metal workpiece without the need for a measurement of the thickness of the workpiece, thus minimizing the potential for human error and inaccuracies in the testing process.

Still a further object of the invention is to use the Joule Effect and the Villari Reversal Point in analyzing the processed signal to more easily determine metallurgical properties of ferrous materials.

BRIEF DESCRIPTION OF THE DRAWINGS

These and other features, aspects, and advantages of the present invention will become better understood with regard to the following description, claims and accompanying drawings where:

FIG. 7 shows the first 57 data points of FIG. 5.

DETAILED DESCRIPTION

Figure 1:
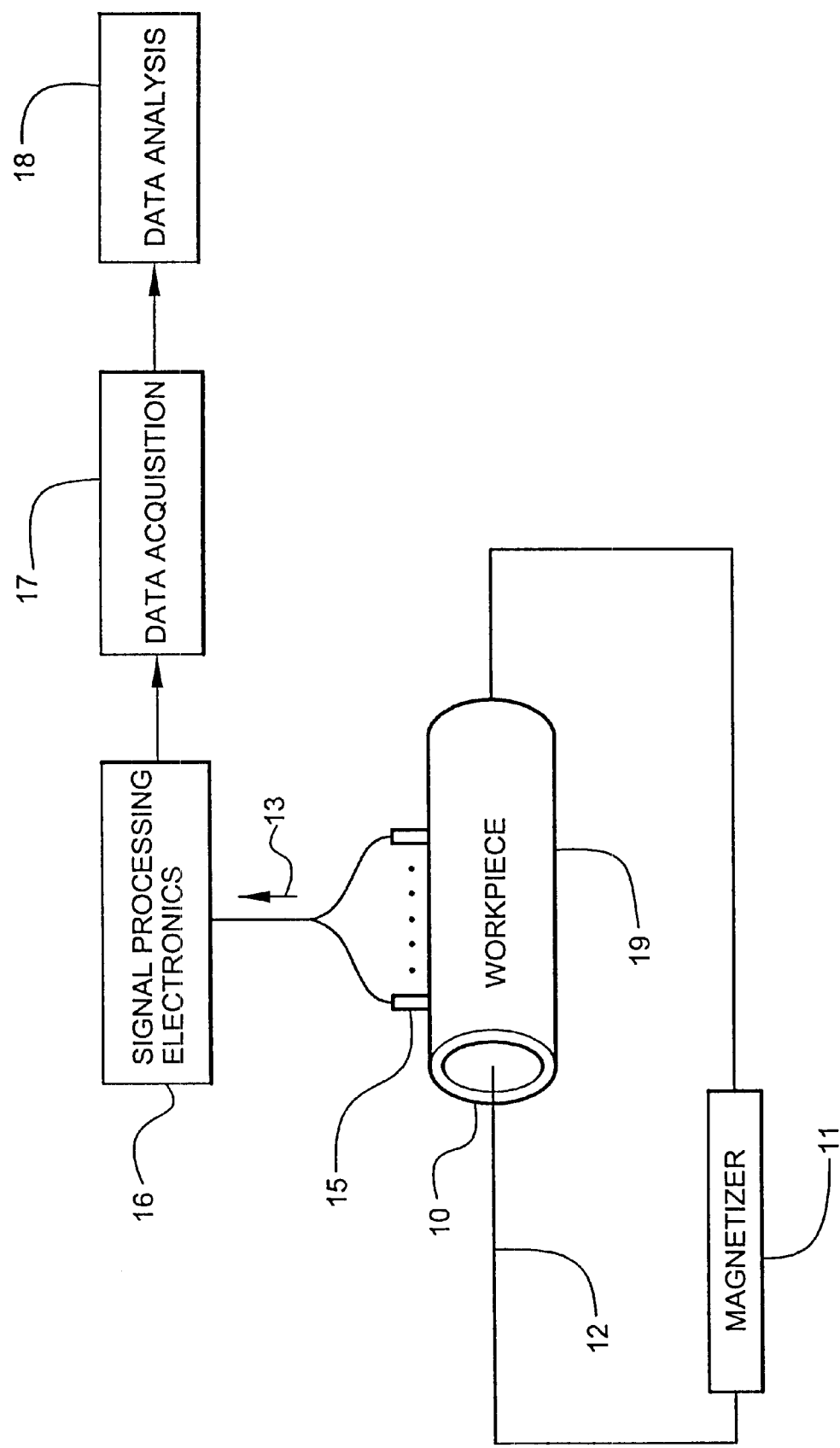
FIG. 1 shows a perspective view of the preferred embodiment of the apparatus in the present invention.

As shown in FIG. 1, the preferred embodiment of the present invention includes a means for inducing a sonic wave into the pipe wall, 10, at least one sensor assembly, 15, signal processing electronics, 16, a data acquisition system 17, and a data analysis system 18. Also shown is a pipe under test, 19. In this embodiment, a sonic wave is induced into the pipe wall by magnetostriction caused by the firing of a capacitive discharge magnetizer, 11, through a central conductor 12 that runs through the pipe 19. The sensor assembly 15 is held in contact with the pipe wall by a spring. The signal from the sensor is carried to the signal processing electronics through a coaxial cable 13. The signal processing electronics 16 are located at a remote site in a cool clean environment.

Figure 3:
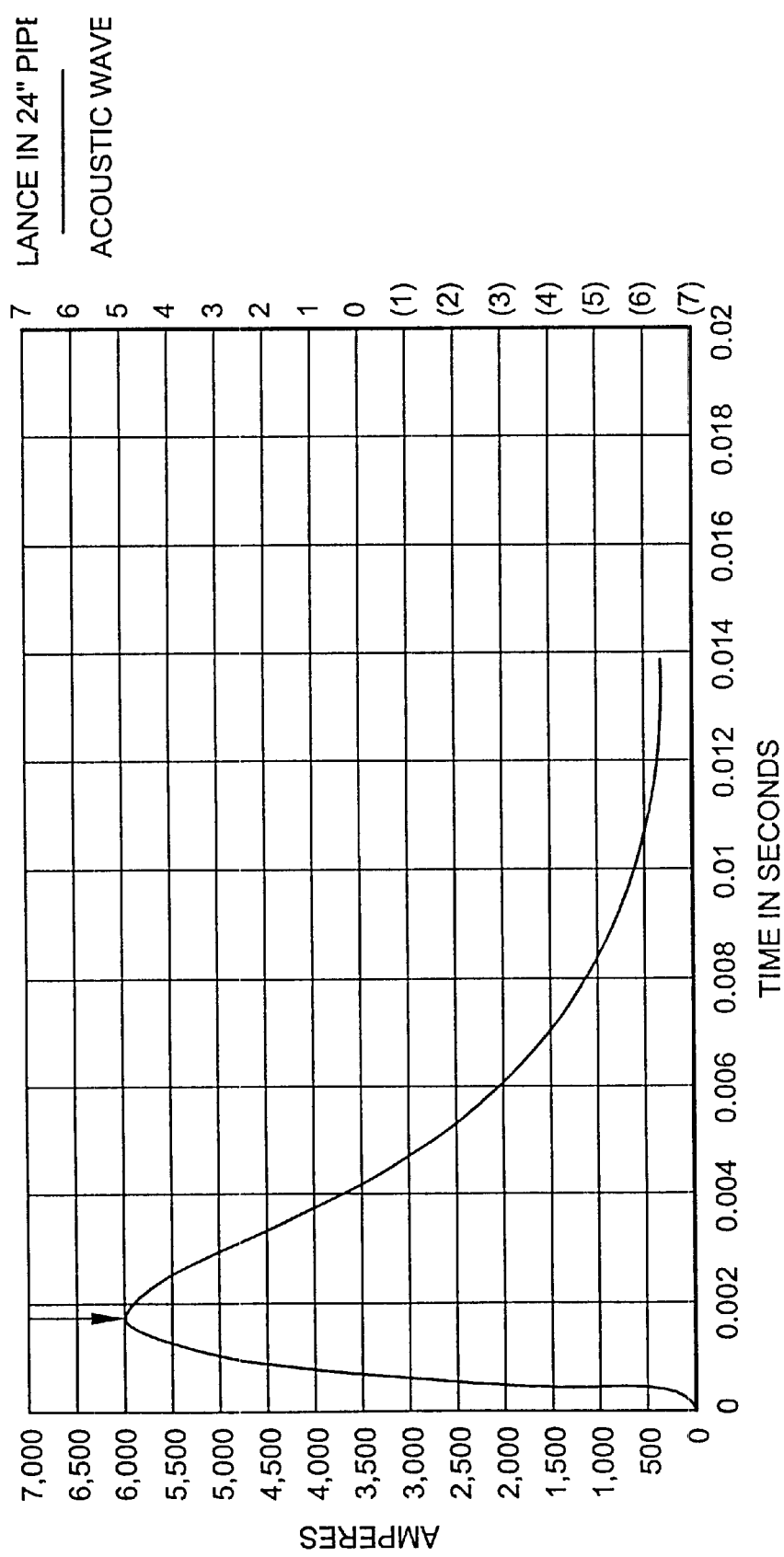
FIG. 3 shows the current discharge through the wire in the center of the pipe in the preferred embodiment of the apparatus in the present invention.

The practice of the preferred embodiment of the present invention begins when the capacitor discharge magnetizer conducts approximately 6000 Amperes of current through an AWG #12 wire 12 that is located along the center axis of the workpiece 19. The discharge lasts for approximately 2 milliseconds and the data is acquired for a total of 500 milliseconds. This period of data allows for the capture of the initial acoustic wave generated by magnetostriction, as well as multiple reflections between the pipe walls. FIG. 3 shows a graphical representation of the current flow 30 thorough the conductor 12. The peak current flow 31 occurs at approximately 2 milliseconds from the time of the initial current discharge.

Figure 2:
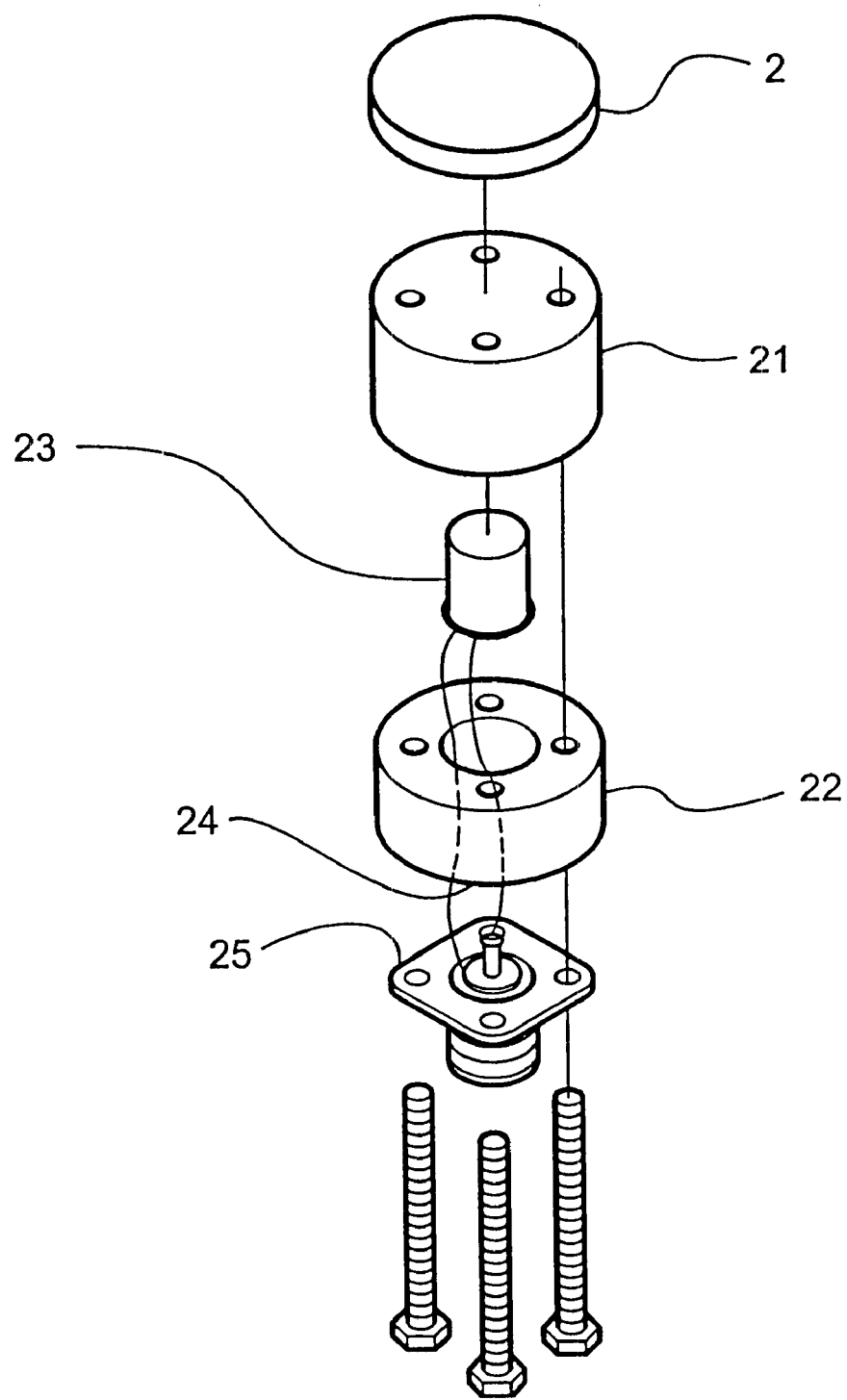
FIG. 2 shows an exploded view of the sensor used in the preferred embodiment of the apparatus in the present invention.

One or more sensors 15 make physical contact with the wall of the pipe 10 being tested so as to be coupled with the acoustic energy. The sensor(s) 15 convert the acoustic energy of the generated wave into electrical energy. FIG. 2 shows an exploded view of the sensor 15 employed in the preferred embodiment of the present invention. The sensor 15 consists of three sections. The first section, 2, is the section that makes contact with the pipe wall surface. This section is made of mild steel, offers wear resistance for the sensor, and is replaceable. The second section of the sensor, 21, is made from acrylic rod. This section electrically isolates the third section, 22, from contact with the pipe surface to insulate the sensor electronics from the large current flow on the pipe surface and prevent damage to the sensor electronics. The third section of the sensor, 22, houses an accelerometer 23, wiring 24, and an electrical connector 25. The third section 22 is machined from aluminum rod and the accelerometer 23 is cemented to the aluminum section. The electrical connector 25 supplies the constant current for excitation and path for signal output through cable 19 to the signal processing electronics. The accelerometer in the preferred embodiment is the Oceana Sensor Technologies, Inc., Model A8000-P01, having a sensitivity of 1000 millivolts/g in a T0–8 package. The accelerometer is mounted in the sensor body so that the axis of highest sensitivity is perpendicular to the surface of the pipe. This mounting arrangement makes the accelerometer most sensitive to the acoustic waves that propagate between the inside and outside surfaces of the pipe walls.

Figure 4:
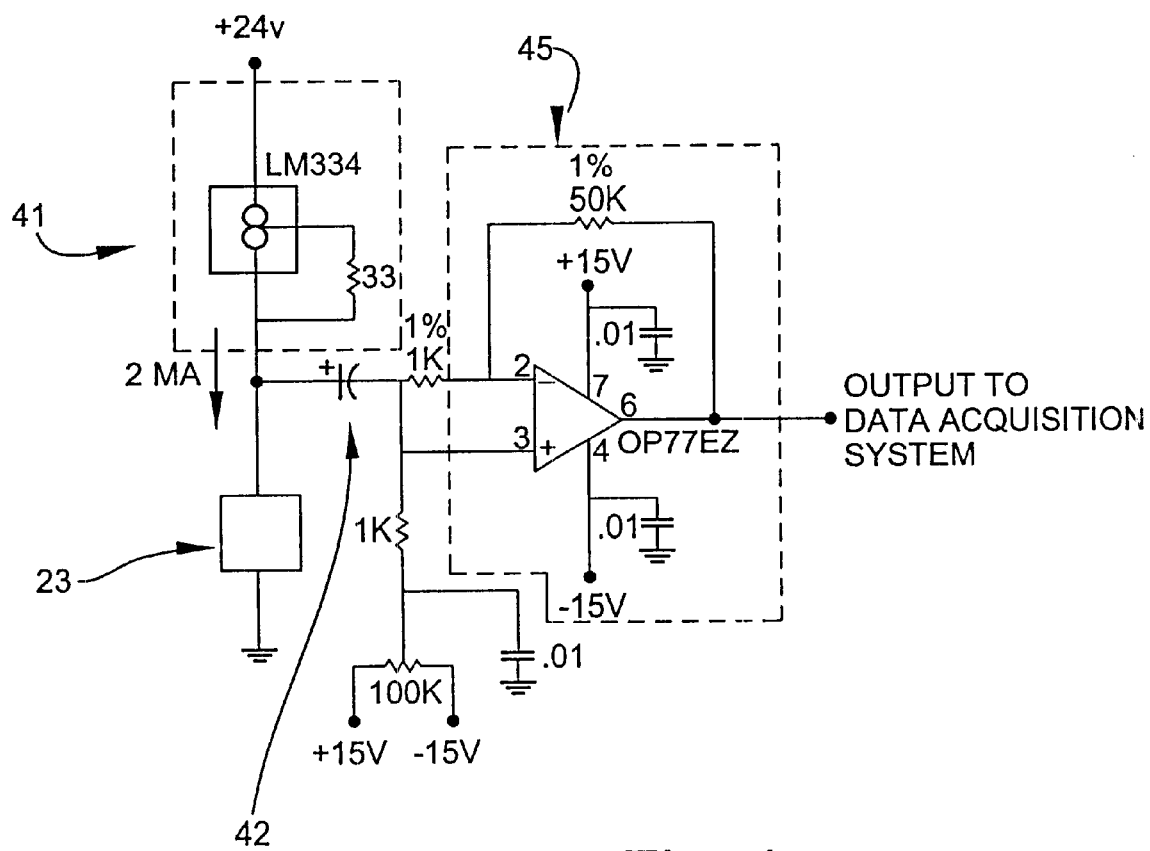
FIG. 4 is a schematic diagram of the signal processing electronics of the preferred embodiment of the apparatus in the present invention.

FIG. 4 depicts the signal processing electronics of the preferred embodiment of the present invention. The signal output from each sensor is sent through the signal processing electronics. An LM334 adjustable current source integrated circuit 41 serves as a constant current source to excite the accelerometer 23. In this embodiment, the excitation current is adjusted for 2 milliamps at 24 volts. The output of the accelerometer is coupled to an amplifier 45 through a 10 microfarad capacitor 42. The capacitor blocks the DC excitation voltage from the amplifier input while allowing the output signal to pass. The amplifier circuit utilizes an OP77EZ low offset operational amplifier, with the gain set at 50. The amplifier 45 increases the voltage of the acoustic signal to a level suitable for the data acquisition system.

The data acquisition system 17 in the preferred embodiment contains a high speed, multiplexed, four channel, 12 bit resolution system. The system resides on a board that plugs into an ISA slot in an IBM-compatible computer. The data acquisition system 17 is synchronized with the magnetizer so that data acquisition begins a few milliseconds before the high current discharge takes place, so that no data is missed. The number of channels in the data acquisition system corresponds to the number of sensors 15 present in the system. In the preferred embodiment, it is desired that one sensor 15 per foot of pipe be used.

Figure 5:
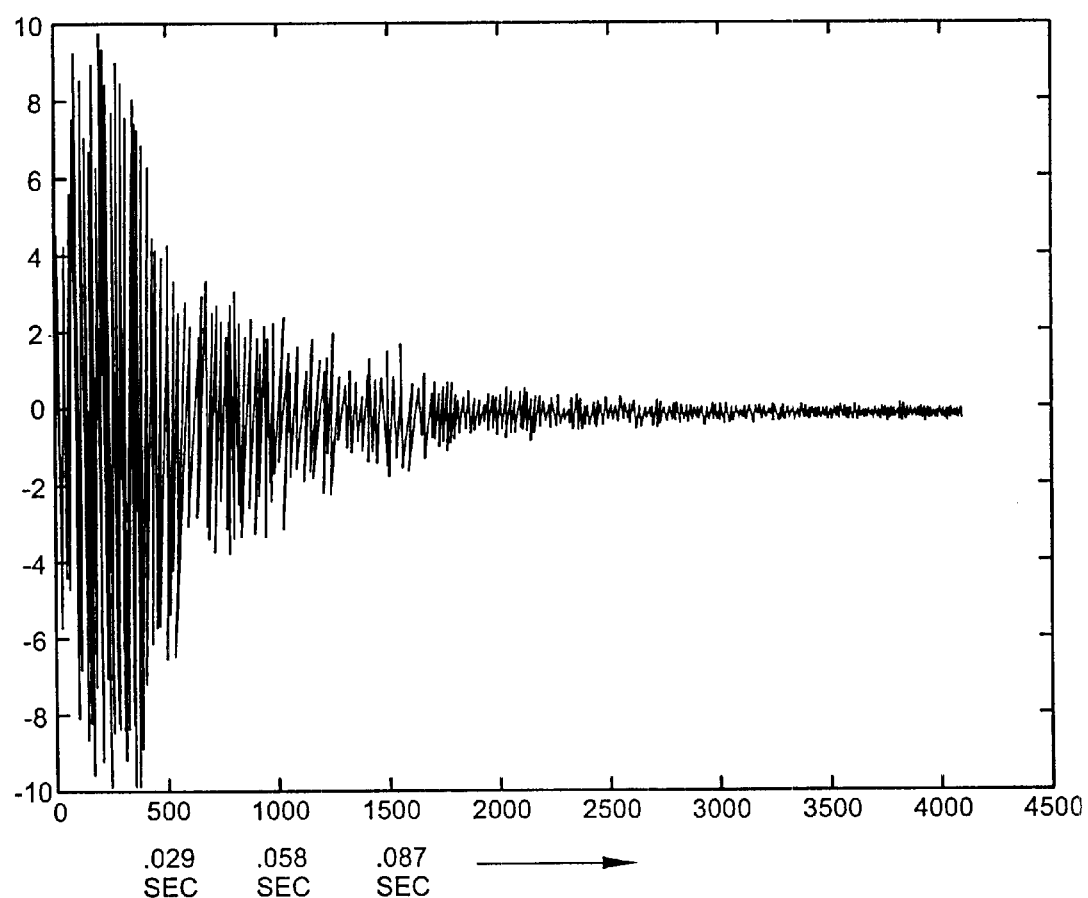
FIG. 5 is a representative data sampling showing the response of a ductile iron workpiece to the excitation of the pipe wall.
Figure 6:
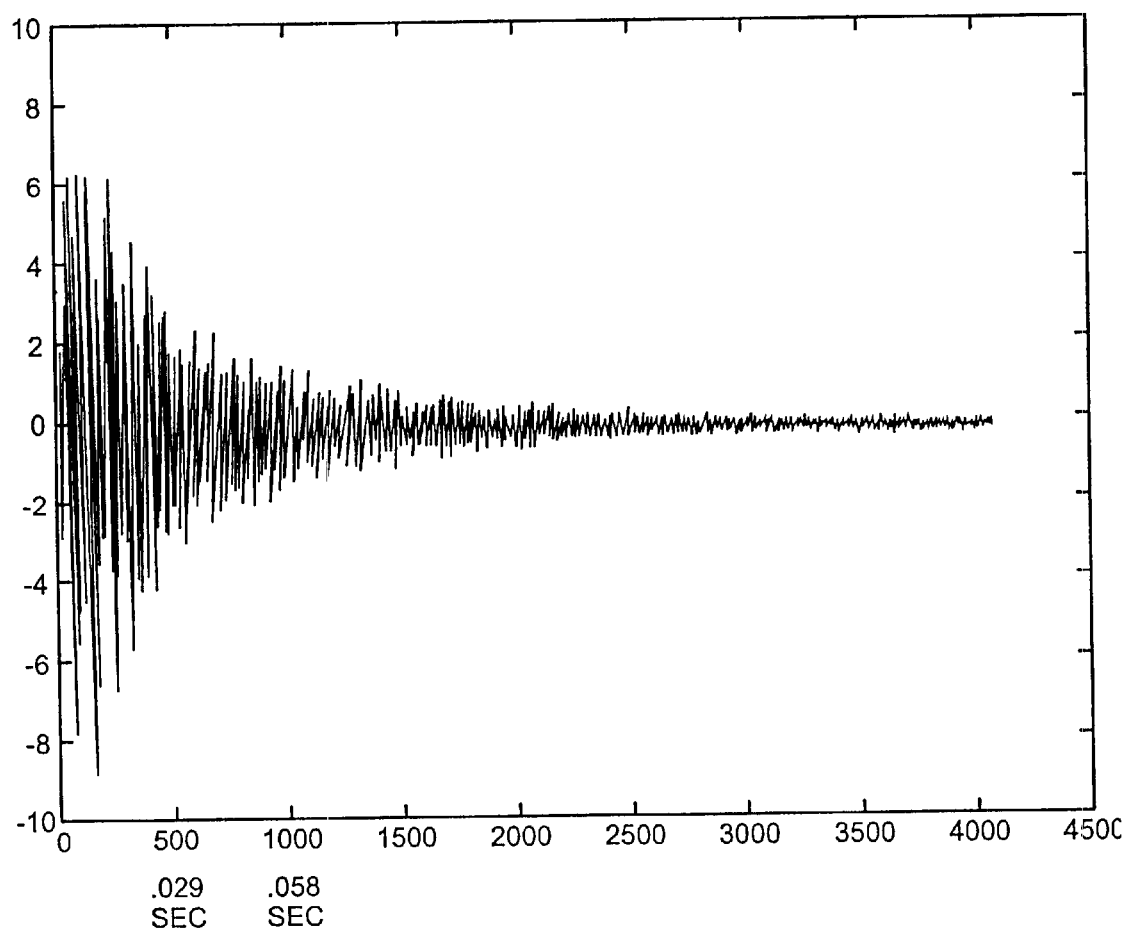
FIG. 6 is a representative data sampling showing the response of a non-ductile iron workpiece to the excitation of the pipe wall.

After its capture by the data acquisition system, the signal is transferred to and analyzed by the data analysis system. The signal, from a 300 millisecond period after the magnetizer discharge, is rectified by the software and any value below the zero baseline is discarded. The peak values of all of the waves are connected to form an envelope. The area under the envelope, representing. the energy associated with the acoustic waves, is calculated, and compared with a known value. Pipe with a high modulus of elasticity, a representative of good nodular microstructure, have high energy, as shown in FIG. 5. Conversely, pipe with a low modulus of elasticity have low energy as depicted in FIG. 6.

Yet another method for determining ductility, without calculating the energy as demonstrated in the first preferred embodiment above, is illustrated below in a second method. The first 57 points of FIG. 5 are illustrated in FIG. 7. This figure shows the graphical representation of the expansion and contraction of the pipe wall as measured by the sensor 15, and processed through the data analysis system. The initial point on the graph is the data reading at the point of the initial current discharge. The waveform represents the measurement of expansion and contraction of the pipe wall caused by magnetostriction. The point 75 at which the waveform crosses the axis is the Villari Reversal Point. At this point, the displacement of the pipe wall crosses the initial rest point, that is, the pipe wall moves from its initial state of expansion to a state of contraction. The Villari Reversal Point 75 moves in time based on the response of the pipe wall to the current discharge. A measurement of time is then made between the initial current discharge 70 and the Villari reversal point 75. A higher measured value indicates good nodular microstructure, while a lower value indicates questionable nodular structure.

Although the present invention has been described in considerable detail with reference to certain preferred embodiments thereof, other embodiments are possible. Upon reading the foregoing disclosure, many variations would be apparent to one skilled in the art. Therefore, the present invention should be defined with reference to the appended claims and their equivalents and the spirit and scope of the claims should not be limited to the description of the preferred embodiments contained herein.

What is claimed is:

1. A non-destructive testing method for determining the microstructure of a ferrous metal object which comprises:

introducing sonic waves into said ferrous metal object;

capturing the intensity of said sonic waves;

converting acoustic energy of said sonic waves into electrical energy;

increasing the voltage of a resulting acoustic signal;

analyzing said signal by plotting a waveform representing the measurement of expansion and contraction of said metal object caused by magnetostriction;

determining a Villari reversal point on the waveform;

measuring a time between an initial current discharge and the Villari reversal point;

comparing said time measurement to a known value.

* * * * *